United States Patent
Matusch (10) Patent No.: US 8,070,713 B2
(45) Date of Patent: Dec. 6, 2011

(54) DISPOSABLE INJECTOR WITH AT LEAST ONE DRAWER HOOK WHICH CAN BE FORCIBLY DECOUPLED

(75) Inventor: Rudolf Matusch, Marburg (DE)

(73) Assignee: LTS Lohmann Therapie Systeme AG, Andernach (DE)

( * ) Notice: Subject to any disclaimer, the term of this patent is extended or adjusted under 35 U.S.C. 154(b) by 35 days.

(21) Appl. No.: 12/653,302

(22) Filed: Dec. 12, 2009

(65) Prior Publication Data

US 2010/0106084 A1 Apr. 29, 2010

Related U.S. Application Data

(63) Continuation-in-part of application No. PCT/EP2008/004950, filed on Jun. 19, 2008.

(30) Foreign Application Priority Data

Jul. 10, 2007 (DE) .......................... 10 2007 032 463

(51) Int. Cl.
*A61M 5/30* (2006.01)
*A61M 5/20* (2006.01)

(52) U.S. Cl. .............................. 604/68; 604/72; 604/135

(58) Field of Classification Search .............. 604/68–72, 604/131, 34, 135–137
See application file for complete search history.

(56) References Cited

U.S. PATENT DOCUMENTS

| | | | |
|---|---|---|---|
| 3,557,784 A * | 1/1971 | Shields | 604/68 |
| 3,625,208 A | 12/1971 | Frost et al. | |
| 4,378,015 A | 3/1983 | Wardlaw | |
| 4,553,962 A | 11/1985 | Brunet | |
| 4,722,728 A | 2/1988 | Dixon | |
| 4,968,302 A | 11/1990 | Schluter et al. | |
| 5,073,165 A | 12/1991 | Edwards | |
| 5,741,229 A * | 4/1998 | Robinson et al. | 604/100.03 |
| 6,258,068 B1 | 7/2001 | Kirchhofer et al. | |
| 6,387,074 B1 * | 5/2002 | Horppu et al. | 604/89 |
| 2006/0129089 A1 | 6/2006 | Stamp | |

* cited by examiner

*Primary Examiner* — Nicholas Lucchesi
*Assistant Examiner* — Leah Stohr
(74) *Attorney, Agent, or Firm* — R. S. Lombard; K. Bach (57) ABSTRACT

A disposable injector with a housing (10) in which at least one mechanical spring energy accumulator (50), at least one cylinder-piston unit (100), at least one piston-actuating ram and at least one release unit are arranged. The housing has at least one draw hook (21) which has at least one supporting surface in the region of its free end. The piston-actuating ram bears against the supporting surface. The blocking position of the draw hook is ensured by a release element positioned in a blocking position. The release (82) has a release position which brings about an inevitable lateral retraction of the draw hook—with the piston-actuating ram being released.

6 Claims, 5 Drawing Sheets

DISPOSABLE INJECTOR WITH AT LEAST ONE DRAWER HOOK WHICH CAN BE FORCIBLY DECOUPLED

CROSS-REFERENCE TO RELATED APPLICATION

This is a continuation-in-part application of pending international application PCT/EP2008/004950 filed Jun. 19, 2008 and claiming the priority of German Application No. 10 2007 032 463.6 filed Jul. 10, 2007.

BACKGROUND OF THE INVENTION

The invention relates to a disposable injector with a housing, in which or on which—respectively at least in certain areas—at least one mechanical spring-energy storage, at least one cylinder-piston unit which can be filled at least occasionally with active ingredient, at least one piston-actuating plunger and at least one actuating unit are arranged, wherein the spring-energy storage includes at least one pre-stressed spring element and wherein at least part of the piston-actuating plunger is positioned between the spring-energy storage and the piston of the cylinder-piston unit.

DE 36 44 984 A1 discloses inter alia such an injector which has a spring-pre-stressed piston-actuating plunger, whereof the rearward plunger rod has elastic draw hooks at its free end. The draw hooks hold the piston-actuating plunger positively firmly on one edge of the injector housing. For this they have only a minimal bearing surface on the housing. To activate the injector the draw hooks are pushed away from the edge holding them. As a result, the spring-pre-stressed piston-actuating plunger advances to complete injection.

U.S. Pat. No. 3,557,784 discloses a reusable injector, onto the housing of which a new cylinder-piston unit is inserted per use. For this purpose, the reusable injector is virtually completely disassembled and re-assembled per use. In order to hold the spring which actuates the piston-actuating plunger, two mutually opposite draw hooks are mounted on the housing of the injector via a respective mechanical pivoting joint. The two pivoting joints are arranged on the outer side of the housing.

US 2006/0129089 A1 discloses a highly complicated, multipart reusable injector. It has a tensioned piston-actuating plunger which is supported on the housing by means of a ring having a plurality of fingers. The supporting takes place with the interconnection of other, separate housing parts.

The object of the present invention is therefore to develop a modular disposable injector which has only a few components for its minimal structural size and guarantees secure mounting and function with easy handling.

SUMMARY OF THE INVENTION

The present invention provides a disposable injector with a housing (10) in which at least one mechanical spring energy accumulator (50), at least one cylinder-piston unit (100), at least one piston-actuating ram and at least one release unit are arranged. The housing has at least one draw hook (21) which has at least one supporting surface in the region of its free end. The piston-actuating ram bears against the supporting surface. The blocking position of the draw hook is ensured by a release element positioned in a blocking position. The release (82) has a release position which brings about an inevitable lateral retraction of the draw hook—with the piston-actuating ram being released.

The invention presents here for example a needle-free disposable injector, whereof the piston-actuating plunger is released with a triggering procedure of the disposable injector. For this purpose, for pre-stressing and holding the spring-energy storage the piston-actuating plunger is held positively by at least one draw hook arranged on the housing or integrated in the housing. The draw hook or the draw hooks are held by an actuating element until the disposable injector is used in their locked position. To trigger the injector the draw hook or the draw hooks are released so that the piston-actuating plunger can move under the effect of the spring-energy storage at least approximately parallel to the centre line of the disposable injector.

BRIEF DESCRIPTION OF THE DRAWINGS

Further details of the invention will emerge from the following schematically illustrated embodiments, in which.

DETAILED DESCRIPTION OF THE PARTICULAR EMBODIMENTS

FIGS. 1 to 4 show a simplified principle of a disposable injector with a permanently loaded spring-energy storage. The disposable injector comprises a housing (10), a cylinder-piston unit (100) pre-filled with e.g. an injection solution, a piston-actuating plunger (60) and a screw compression spring (50) as spring-energy storage. Also, an actuating element (82) and a retention element (95) are arranged on the housing (10).

Figure 1:
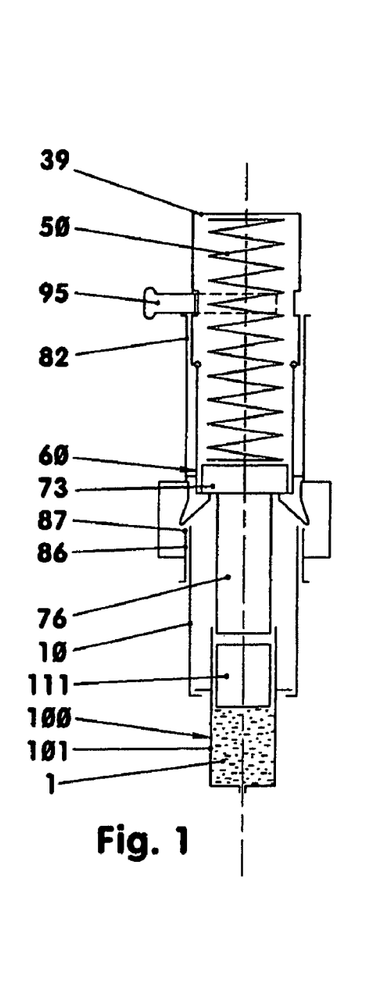
FIG. 1 illustrates a disposable injector with two positively uncouplable draw hooks.

The housing (10) is a pot-shaped hollow body, open at the bottom and with an elevated floor (39). The housing (10) has e.g. two opposite window-like openings (33) in the middle region, the jacket region (31). Articulated on the respectively upper edge of an opening (33) in each case is a draw hook (21). Both draw hooks (21) hold the piston-actuating plunger (60) on its plunger disc (73) in its pre-stressed position. For this purpose, the draw hooks (21) encompass with their relatively large support surfaces (23) the lower front end (74) of the plunger disc (73). The size of the respective contact surface between a support surface (23) and the corresponding front end face (74) is in the region of 10 to 20 mm$^2$.

An inner surface (26) abuts the support surfaces (23) aligning with the centre line (5) in each case. The latter merges here into a frustoconical or conical surface (25), which can also be spherically curved.

On the side averted from the centre line (5) each draw hook (21) has a contact surface (24).

Located in the rear region of the housing (10) is an annular groove (38) for taking up the retention element (95). In the lower region of the housing (10) are holders for fastening the cylinder-piston unit.

In the embodiment the cylinder-piston unit (100) comprises a cylinder (101) filled with an injection solution (1), in which a piston (111) sits in the rear position. Above the piston (111) in the housing (10) the piston-actuating plunger (60) is e.g. arranged such that although it does not touch the piston, it is guided sideways by its lower end in the upper region of the cylinder (101).

According to FIG. 1 the housing (10) is enclosed by the sleeve-like actuating element (82) under the annular groove (38). The actuating element (82) is mounted to move lengthways on the radial outer surface (13) of the housing (10). It has a circumferential widened region (83) in the lower region at the level of the hook ends, as in FIG. 4. There can also be partially widened regions or uncovered openings instead of this widened region (83) in the case of a non-rotating symmetrical actuating element (82) per draw hook (21).

Figure 4:
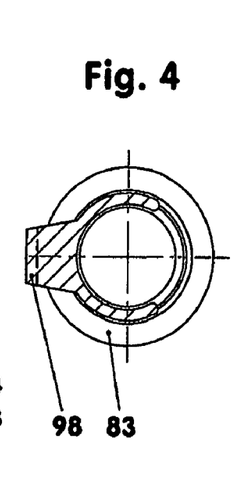
FIG. 4 illustrates the cross-section as in FIG. 1 in the vicinity of the retention element.

With respect to the housing (10) the widened region (83) is positioned and dimensioned so precisely that it can take up the outwardly thrust draw hooks (21) which retract during the actuating operation. The inner contour of the widened region (83) is a channel with a return flank (84), which here represents a plane normal to the centre line (5) of the injector. The transition between for example the cylindrical inner wall of the actuating element (82) and the return flank (84) is configured e.g. as a sharp edge (85).

Figure 2:
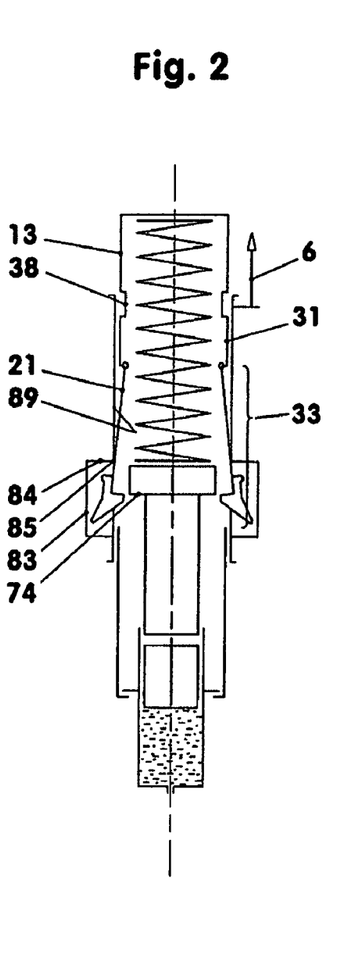
FIG. 2 as for FIG. 1, but unlocked and actuated.
Figure 3:
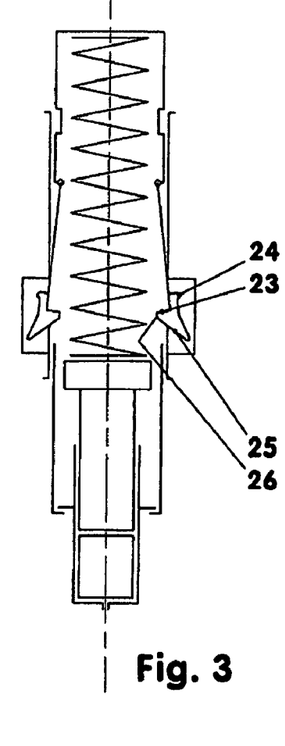
FIG. 3 as for FIG. 2, but following drug ejection.

Opposite the return flank (84) is a release flank (86) which has a release edge (87) which encompasses the draw hook ends at least in certain areas, according to FIGS. 1 to 3. In FIG. 1 the release edges (87) do not contact the draw hooks (21). The wall of the sleeve-like actuating element (82) bearing the release edge (87) here likewise slides on the outer wall (13) of the housing (10).

According to FIG. 1 the draw hooks (21) lie securely with their outermost contact surfaces (24) on the inner wall (89) of the actuating element (82). In FIGS. 2 and 3 the release edges (87) contact the frustoconical or conical flanks (25) of the draw hooks (21).

The piston-actuating plunger (60) arranged in the housing (10) is here divided into two regions. The lower region is the piston slide (76). Its diameter is slightly smaller than the inner diameter of the cylinder (101) of the cylinder-piston unit (100). The lower front end of the piston slide (76) acts directly on the piston (111).

The upper region, the plunger disc (73), is a flat disc, cylindrical at least in certain areas, whereof the outer diameter is a few tenths of a millimeter smaller than the inner diameter of the housing (10) in the jacket region (31).

The piston slide (76) can of course also be designed as a separate component, separate from the plunger disc (73). For this purpose it is placed on the inner wall of the housing (10).

The screw compression spring (50) sits pre-stressed between the plunger disc (73) and the elevated floor (39) of the housing (10).

As per FIG. 1 the actuating element (82) bears on a retention element (95) which sits in the annular groove (38). The retention element (95) is for example an elastic omega-shaped bail which resiliently encloses the annular groove (38) of the housing (10) at an angle of ca. 120 degrees of angle. As in FIGS. 1 and 4 it has on the left side a handle (98), via which it can be laterally removed for unlocking.

To activate the disposable injector—after removal of a nozzle seal—the retention element (95) is first drawn to the side. Then the actuating element (82) is gripped with the hand formed into a fist and the disposable injector is positioned at the injection site. At this point the thumb is located at the rear end of the disposable injector. It lies on the floor (39) of the housing (10). For immediate release the thumb of the hand holding the disposable injector is pressed against the floor (39). With this procedure the actuating element (82) slides to the rear on the outer wall (13) of the housing (10), thus away from the injection site. The contact surfaces (24) of the draw hooks (21) slip over the edge (85) and are thus unlocked. At the same time or shortly after the release edge (87) contacts the frustoconical surface (25). Due to the upward movement (6) of the actuating element (82) the release edge (87) pushes the respective draw hook (21) over the frustoconical surface (25) almost radially outwards, as in FIG. 2. The release edge (87) of the actuating element (82) and the frustoconical surface (25) of the individual draw hook (21) together form respectively a positive spline gear.

The draw hook end deviates into the widened region (83) and in the process releases the plunger disc (73). Now the piston-actuating plunger (60) can shoot down unhindered as in FIG. 3. The cylinder (101) is emptied.

FIGS. 5 to 8 show an embodiment of the principle described in FIGS. 1 to 4. Here the load-bearing component is a two-piece housing (10). It is made from two e.g. identical half shells (11, 12), whereof the assembly joint lies in a plane laid on the centre line (5). Both half shells are made e.g. from a fibreglass-reinforced polyamide by injection moulding. In the assembly area each half shell has at least one raised link (18) and e.g. four trunnions (19), as in FIGS. 7 and 8. After both parts are stuck together, the trunnions (19) and the link (18) of one half shell (11) engage in corresponding recesses of the other half shell (12).

The mounted housing (10) has an extensively tubular shape and is divided into three functional areas (16, 31, 41). As in FIGS. 5 and 6 the upper area is the release region (16). The jacket region (31) is attached thereto. Arranged between both areas is a false floor (32). The false floor (32) has a central recess (34).

A closed floor (39) is located in the release region (16) above the false floor (32). Between both floors (32, 39) the outer wall of the housing (10) has two circumferential links (37). The annular groove (38) laid between the links (37) serves to receive a retention element (95), as in FIG. 5.

Figure 7:
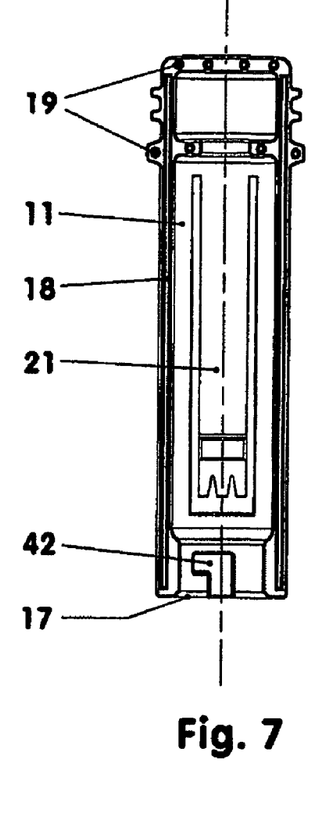
FIG. 7 shows an inner view of half a housing of the disposable injector, as in FIG. 5.
Figure 8:
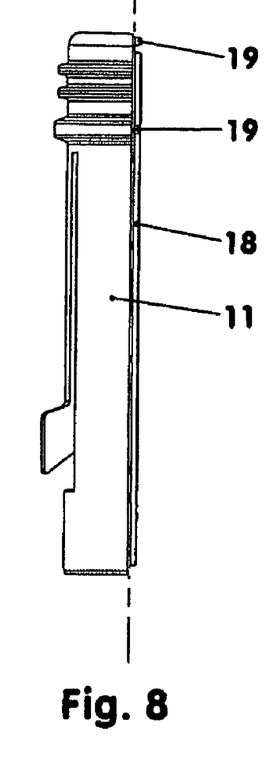
FIG. 8 shows a side elevation to FIG. 7.

In the jacket region (31) of each half shell (11, 12) is a formed draw hook (21), as in FIGS. 7 and 8 also. The forming site for the draw hooks (21) is just under the false floor (32), where the outer wall of the housing (10) has a circumferential support link (36).

For forming the respective draw hook (21) there is located in the jacket section (31) a narrow, at least approximately U-shaped gap. The upper region of the draw hook (21), corresponding to ca. 80% of the length of the draw hook (21), corresponds to the wall of the housing (10) with respect to the wall thickness and curvature. This region functions as a spring-elastic flexional beam (22) and has a sickle-shaped cross-section.

If required, part of this flexional beam (22) can also be equipped with a rectangular cross-section to reduce bending stresses occurring from use in the flexional beam edge region. In FIGS. 7 and 8 the draw hook (21) is shown in the undeformed state.

The here lower free end of the individual draw hook (21) is designed as a hook with at least three functional surfaces (23, 24, 25). A surface which can be wrapped around for a hook forms the support surface (23), on which the piston-actuating plunger (60) rests via its lower front end (74) when the disposable injector is stressed. If required, the draw hooks (21) have ceramic armour at least in the vicinity of the support surfaces (23).

Figure 5:
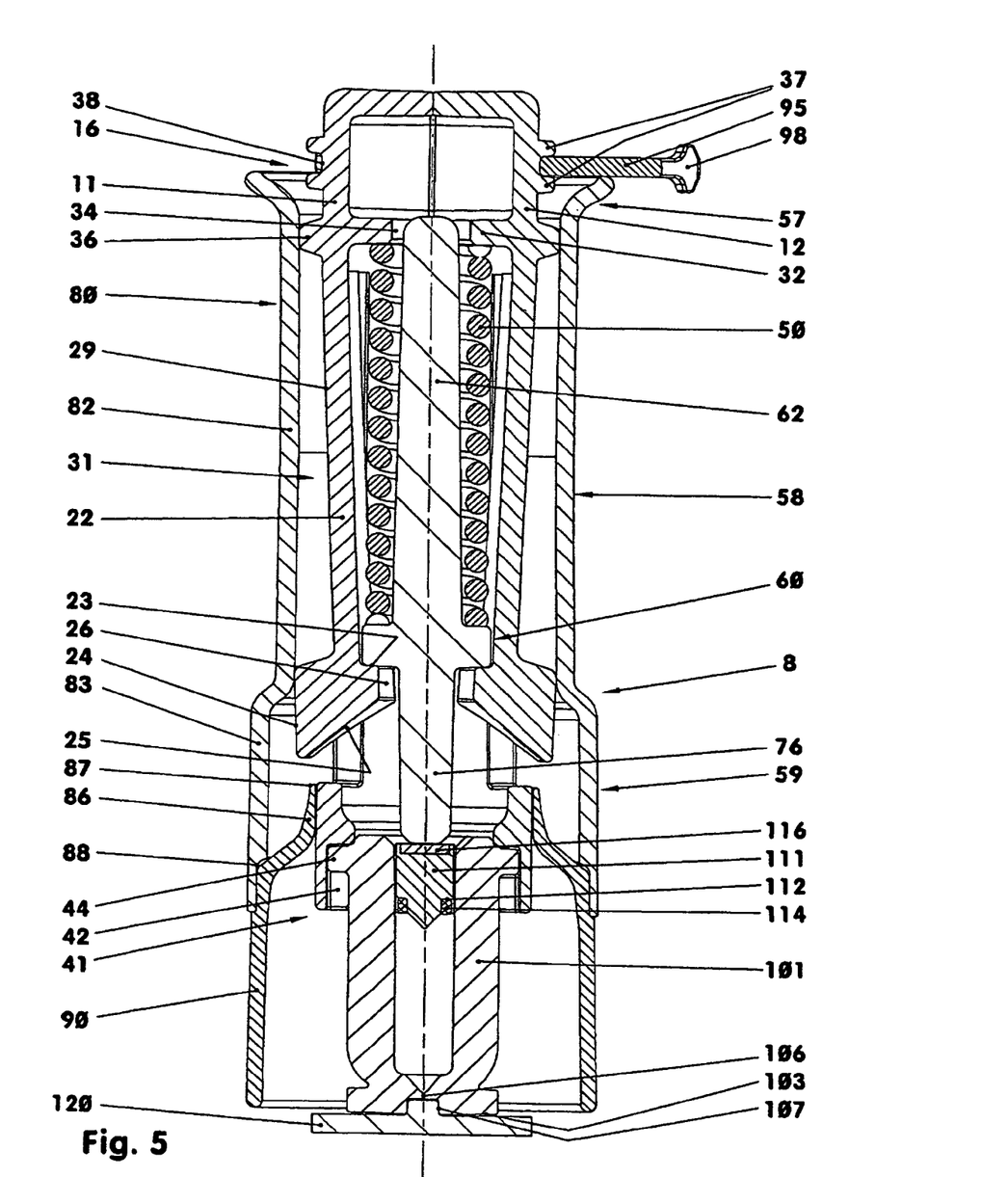
FIG. 5 illustrates a disposable injector with two draw hooks deformed in locked position.

The downward oriented face of the draw hook (21) is the so-called frustoconical surface (25). The frustoconical surfaces (25) of both deformed draw hooks (21), as in FIG. 5, are sections of an envelope of a cone, whereof the tip lies on the centre line (5) in the region of the plunger disc (73). The imaginary envelope of a cone here has e.g. a conical angle of 100 degrees of angle.

Attached to the frustoconical surface (25) is the radially outward aligned contact surface (24). According to FIGS. 6 and 8 the contact surface (24) projects by e.g. 1.6 times the flexional beam wall thickness radially outwards over the outer wall of the housing (10).

As in FIG. 7 the lower end of the draw hook (21) has e.g. two notches.

The fixing region (41) for taking up the incorporable cylinder-piston unit (100) is located under the jacket section (31). The fixing region (41) is part of a bayonet socket. For this purpose two or more angular channels (42) are arranged on its inner wall, as in FIG. 7. The channels (42) lead vertically up from the lower housing front end (17) and merge respectively into a short horizontal channel section after a few millimeters.

In the fixing region (41) the cylinder (101) is set and fixed via e.g. two or more bayonet catches (44), as in FIG. 5. One or more latching elements, which prevent the bayonet socket from releasing, and thus the cylinder (101) from being removed, are located where required in the horizontal channel section or on at least part of the bayonet catches (44).

In the fixing region (41) the cylinder (101) is set and fixed via e.g. two or more bayonet catches (44), as in FIG. 5. One or more latching elements, which prevent the bayonet socket from releasing, and thus the cylinder (101) from being removed, are located where required in the horizontal channel section or on at least part of the bayonet catches (44).

The cylinder (101) is e.g. a thick-walled pot. In the for example cylindrical bore of the cylinder (101) sits the rod-less piston (111). On its front at least approximately frustoconical front end the piston (111) has an axial annular groove (112) for receiving a sealing ring (114) or a permanently elastic sealing mass. An e.g. cylindrical metal plate (116) is set into the rear front end of the piston (111).

Located in the centre of the bore of the cylinder (101), whereof the cylinder floor matches the contour of the front piston front end at least approximately, is a short cylindrical, nozzle-like bore (106). Its diameter is ca. 0.1 to 0.5 millimeters. This bore (106) is one to five times as long as its diameter. It ends in a cylindrical recess (107) of the floor-side outer front end (103) of the cylinder (101).

The spring-energy storage (50) or respectively the drive unit of the disposable injector is arranged between the piston (111) and the false floor (32). The spring-energy storage (50) is a screw compression spring, arranged on the piston-actuating plunger (60) with the plunger disc (73). The resilience-stressed piston-actuating plunger (60) is supported on the draw hooks (21) of the housing (10) by means of the plunger disc (73).

Above the plunger disc (73) the piston-actuating plunger (60) has a pilot pin (62) which guides the screw compression spring (50). Located centrally under the plunger disc (73) in the extension of the pilot pin (62) is a piston slide (76), which acts on the piston (111) when the disposable injector is activated.

The actuating element (82) partially enclosing the housing (10) and the cylinder-piston unit is here likewise a release sleeve. The rotationally symmetrical release sleeve (82), made of acrylontrile butadiene styrene know as ABS plastic for instance, has three regions, an insertion region (57), a middle region (58) and a widened region (59). The middle region (58) can be an at least approximately cylindrical pipe. In the embodiment it comprises two almost identically long frustoconical pipe sections which widen out upwards and downwards from their geometric middle, as in FIG. 5. The respective conical angle is e.g. 2° of angle.

In FIG. 5 the funnel-shaped widening insertion region (57) attaches at the top to the middle region (58) and has a conical angle of 100 to 110 degrees of angle. The maximal diameter of the insertion region (57) is greater than the maximal outer diameter of the mounted housing (10) in the region of the lower ends of the draw hooks (21).

The widened region (59) borders the middle region at the bottom. It is likewise a slightly frustoconical pipe section, of which the cross-section enlarges continuously downwards. Its conical angle is ca. 2 degrees of angle. Located between the middle region (58) and the widened region (59) is a transition area. Because at this point the widened region (59) has a diameter which is larger by ca. two release sleeve wall thicknesses than the outer diameter of the adjoining middle region (58), the transition area forms a shoulder there.

The lower edge of the widened region (83) has a turned groove (88), in which a splitter protective pipe (90) made e.g. from polycarbonate (PC) or polymethyl methacrylate (PMMA) sits glued or welded. The transparent splitter protective pipe (90), which to a large extent encloses the cylinder-piston unit (100), tapers to the housing (10) at least approximately funnel-like to the extent where its inner wall contacts the outer wall of the housing (10) with clearance. The upper leading edge of the splitter protection (90) lying in this area is here the annularly circumferential release edge (87) attached to the release flank (86). Underneath the release edge (87) the release flank (86) has a conical angle of less than 60 degrees of angle.

Figure 6:
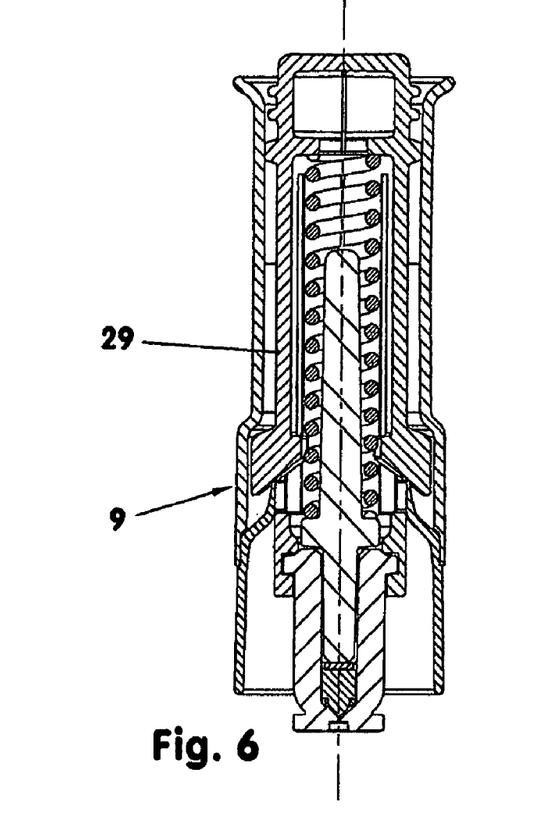
FIG. 6 as for FIG. 5, but unlocked and actuated.

FIG. 6 shows the disposable injector without retention element (95), thus unlocked, with elevated actuating element (82).

With elevating the actuating element (82), which can also be designated as depressing the housing (10), the contact surfaces (24), as in FIG. 5, slide outwards along the return flank (84). The outward bending of the draw hooks (21) is enforced as soon as the hook-side frustoconical surfaces (25) compulsorily glide along the edge (85), thus the upper edge (87) of the splitter protection (90). The draw hooks (21), now no longer deformed, now release the piston-actuating plunger so that the piston (111) is abruptly pushed back into the cylinder (101).

FIGS. 11 to 14 illustrate further forced unlocking for a draw hook injector. Here the draw hooks (21) are thrust outwards by the piston-actuating plunger (60) by means of an expandable gear integrated in the actuating unit (80).

For this the injector has a special piston-actuating plunger (60). Above the piston slide (76) it is at least in certain areas designed hollow. It has a central bore (68), whereof the middle line e.g. coincides coextensively with the centre line (5). The bore (68) in the plunger disc (73) ends in a recess (63) having two opposing, e.g. radial, openings (64), as in FIG. 12. In the region of the plunger disc (73) the piston-actuating plunger (60) is e.g. subdivided for production reasons. The piston slide (76) has two barbs (77), with which it e.g. undetachably snap-locks in corresponding recesses (72) of the plunger disc (73), as in FIG. 11.

Figures 9, 10, 11, 12:
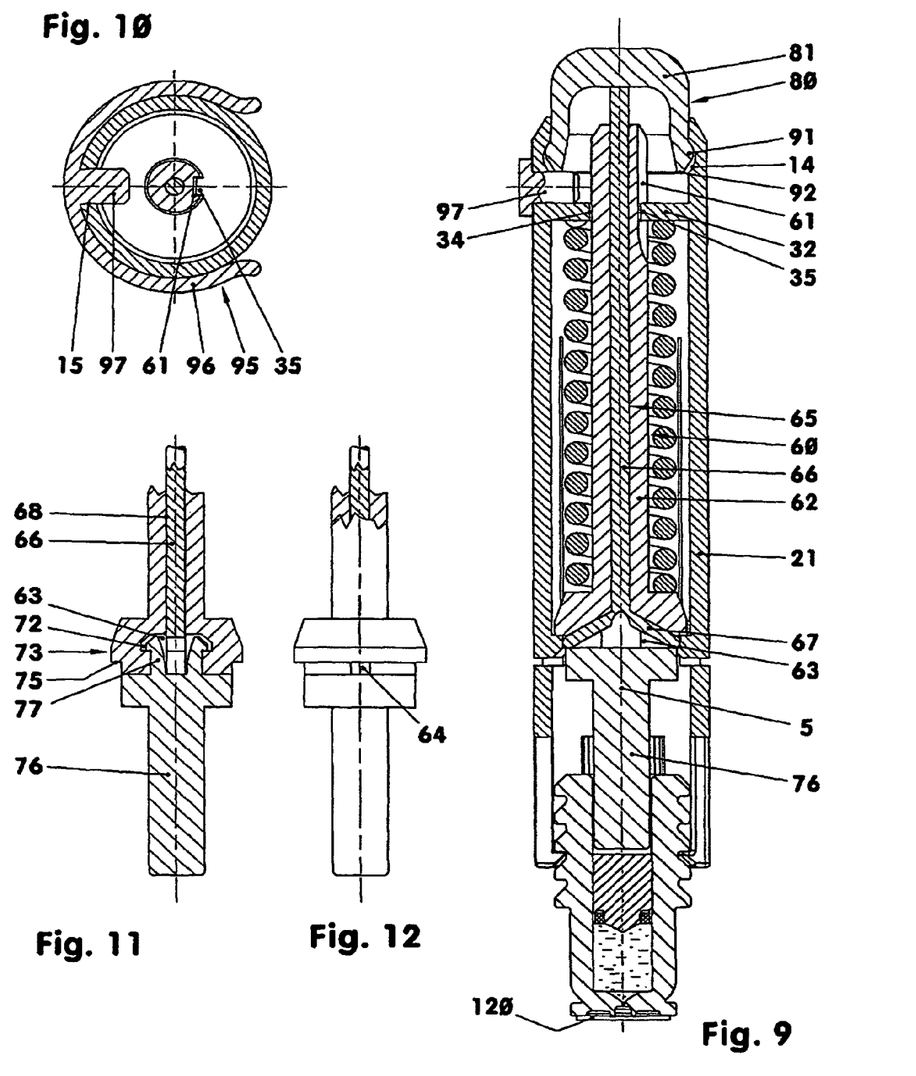
FIG. 9 illustrates a disposable injector with two draw hooks deformed in actuating position.
FIG. 10 illustrates the cross-section as in FIG. 9 in the vicinity of the retention element.
FIG. 11 is a partial longitudinal view through the piston-actuating plunger.
FIG. 12 is a partial view of the piston-actuating plunger (fictitious state)

In the vicinity of the openings (64) the plunger disc (73) has a collar face (75), circumferential at least in certain areas and oriented normally to the centre line (5). The draw hooks (21) bear with their support surfaces (23) on this collar face (75).

A forked compression rod (65) is inserted in the bore (68) and the recess (63). The compression rod (65) here has a cylindrical shaft (66), guided in the bore (68) with clearance. Articulated on the lower end of the shaft (66) are two pendulum rods (67). The pendulum rods (67) have e.g. a rectangular cross-section. The links between the shaft (66) and the pendulum rods (67) are for example film links. Where required, only the pendulum rods (67) are joined together and the shaft forms a separate component.

According to FIG. 9 the pendulum rods (67) of the compression rod (65) in the unactuated injector form the equilength legs of an isosceles triangle. The free ends of the pendulum rods (67) bear on the respective inner surfaces (26) of the draw hooks (21), as in FIG. 14.

The upper, free end of the compression rod (65) projects up out of the bore (68). A pushbutton (81) bears with its floor on the front end of the shaft (66).

The pushbutton (81) in principle has the form of a can, comprising a floor and flashing. On the outside in the lower region it has at least two radially protruding cams (91). The cams (91) engage in depressions (14) of the housing (10) when the pushbutton (81) is installed and secured, as in FIG. 9.

The flashing has a lower, e.g. even edge (92), serving as stop against the false floor (32) of the housing (10) when the pushbutton (81) is activated. In the unactuated and secured state the edge (92) lies on a locking pin (97) of a retention element (95).

The retention element (95) comprises the locking pin (97) and an open spring-loaded ring bearing the latter in the form of an omega spring (96), as in FIG. 10. On the secured injector the omega spring (96) sits on the outer wall of the housing (10), enclosing the outer wall at ca. 240 degrees of angle. The locking pin (97) enters a bore (15) of the housing (10) and projects a few millimeters into the housing interior, as in FIG. 9. If needed, at least one of the free ends of the omega spring (96) is sealed with a paper or film banderole.

To align the piston-actuating plunger (60) relative to the housing (10) the false floor (32) projects with rotation prevention (35) into a guide groove (61) of the piston-actuating plunger (60). For rotation prevention the cross-section of the piston-actuating plunger (60) and the bore (34) can also be designed rectangular, oval, elliptical or the like.

Figure 13:
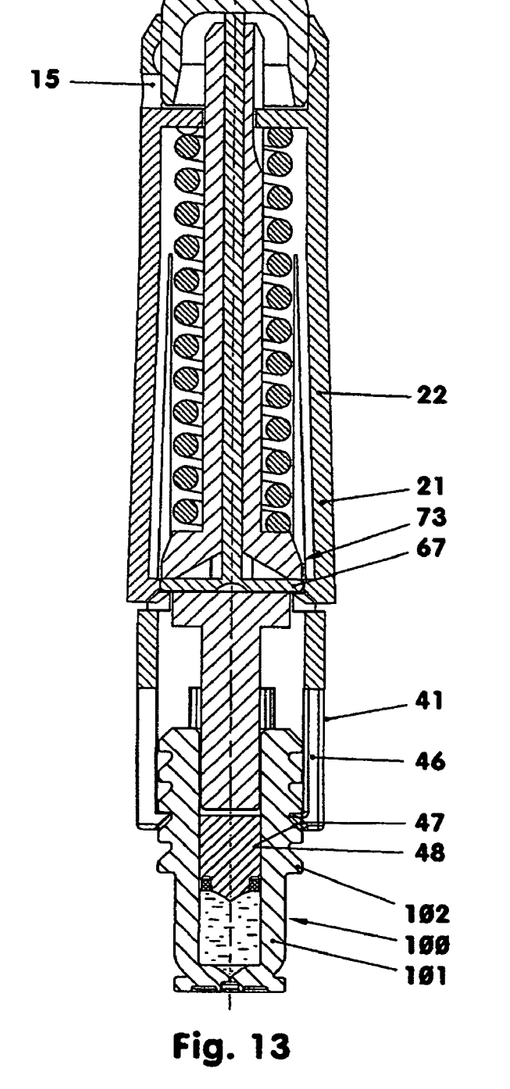
FIG. 13 as for FIG. 9, but unlocked and actuated.

In the lower region of the housing (10), as in FIG. 13, is the fixing region (41) for receiving the incorporable cylinder-piston unit (100). The fixing region (41) includes e.g. six spring hooks (46), which in each case terminate in an inwards aligned hook tip (47). The hook tips (47) have chamfering (48) extending over the entire hook thickness to the lower housing front end. The length and resiliency rate of the spring hooks (46) is dimensioned such that the internal fittings (50, 100) required for function of the disposable injector can be incorporated without plastic deformation of the spring hooks (46).

The cylinder (101) of the cylinder-piston unit (100) is here a thick-walled pot, whereof the optionally cylindrical outer wall bears for example five circumferential detent ribs (102). The sum of the detent ribs (102) has in cross-section e.g. a saw-tooth profile, wherein the division between the toothed detent ribs (102) is equidistant. The maximal diameter of the detent ribs (102) is slightly less than the inner diameter of the housing (10) in the fixing region (41). The diameter of the regions lying between adjacent detent ribs (102) corresponds to the minimal diameter of the housing (10) in the vicinity of the hook tips (47).

To actuate the injector the pushbutton (81) is pressed down after lateral withdrawal of the retention element (95) and removal of the protective film (120), as in FIG. 9. At this point, the pendulum rods (67) slide-pushed by the downwardly moved shaft (66)—into a stretch position, as in FIG. 13. The free ends of the pendulum rods (67) press the draw hooks (21) elastically deforming outwards so that they no longer encompass the plunger disc (73).

Figure 14:
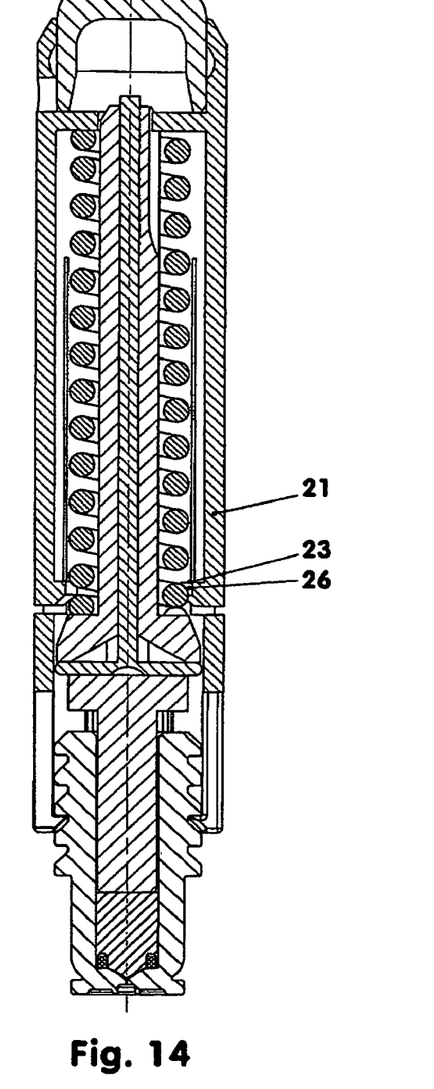
FIG. 14 as for FIG. 13, but following drug ejection.

The spring element (50) now thrusts the piston-actuating plunger (60) down, as in FIG. 14. The injection procedure is completed with ejection of the drug via the cylinder-piston unit (100).

With injectors, in which, as in the previously described variant, the piston-actuating plunger (60) is guided straight at least in the bore (34) of the floor or false floor (32), and the piston-actuating plunger (60) has adequate bending strength, only a single draw hook (21) can be used instead of two or more draw hooks (21).

In the variants illustrated in the figures the individual contact zone between the draw hook (21) and the plunger disc (73) is designed as surfaces (23) and (74, 75), which contact each other in a glidable manner. In a particular configuration in each surface (23) of the individual draw hooks (21) a roller can be mounted, which rolls away as a roller bearing, therefore with low friction, when the injector is actuated on the surface (74, 75) of the plunger disc.

With the exception of the spring element (50), and where required the available piston plate (116), all parts of the previously described disposable injectors are made of plastics or plastics or rubber-like materials.

LIST OF REFERENCE SYMBOLS 1 injection solution; drug
5 centre line of the disposable injector
6 actuation direction of movement of (82), upwards movement
8 locked position
9 actuating position
10 housing, one-piece
11 first half shell
12 second half shell
13 outer surface, cylindrical
14 depressions, annular groove
15 bore
16 release region, top
17 lower housing front end
18 link
19 trunnion
21 draw hook
22 flexional beam
23 support surface
24 contact surface
25 frustoconical, conical surface
26 inner surface
29 rear surface
31 jacket region
32 false floor
33 openings
34 bore
35 rotation prevention
36 support link
37 links, circling outwards
38 annular groove for (95)

39 floor
41 fixing region for cylinder-piston unit
42 channels, angular
44 bayonet catch
46 spring hooks
47 hook tip
48 chamfering
50 spring element, screw compression spring, spring-energy storage
57 insertion region
28 middle region
29 widened region
60 piston-actuating plunger
61 guide groove
62 pilot pin
63 recess
64 openings, radial
65 compression rod, forked
66 shaft
67 pendulum rods
68 bore
72 recesses in (73)
73 plunger disc
74 front end, below; front end face
75 collar face; front end face
76 piston slide
77 barbs on (76)
80 actuating unit
81 pushbutton
82 actuating element
83 widened region
84 return flank
85 edge, sharp-edged
86 release flank
87 release edge
88 turned groove, housing collar
89 inner wall
90 splitter protective pipe
91 cams
92 edge, below
95 retention element
96 omega spring
97 locking trunnion, locking pin
98 handle
100 cylinder-piston unit
101 cylinder
102 detent ribs, outside; outer fluting
103 front end
106 bore, nozzle
107 recess in front end
111 piston
112 annular groove
114 sealing ring, seal
116 metal plate, magnetic or magnetisable
120 protective film, adhesive seal

What is claimed is:

1. A disposable injector comprising:
a housing (10), in which or on which—respectively at least in certain areas—at least one mechanical spring-energy storage,
at least one cylinder-piston unit (100) which can be filled at least occasionally with active ingredient,
at least one piston-actuating plunger (60) and at least one actuating unit (80) are arranged,
a spring-energy storage (50) includes at least one pre-stressed spring element,
at least part of the piston-actuating plunger (60) is positioned between the spring-energy storage (50) and a piston (111) of the cylinder-piston unit (100),
the housing (10) has at least one draw hook (21) having at least one support surface (23) respectively in the region of its free end,
the piston-actuating plunger (60) rests on the support surface (23),
the piston actuating plunger (60) has a longitudinal central bore (68) and the plunger (60) has a plunger disc (73) proximate one end thereof, the actuating unit (80) includes a compression rod (65) having a shaft (66) in slideable relationship with the bore (68), two pendulum rods (67) are articulated on or proximate the lower end of the shaft (66), at least a part of the actuating unit (80) including the compression rod (65) and the pendulum rods (67) are guided and supported in the piston-actuating plunger (60), and
wherein the actuating unit (80) has an actuating position (9) which causes lateral outward pushing of the at least one draw hook (21) for releasing the piston-actuating plunger (60).

2. The disposable injector according to claim 1, wherein actuating unit (80) includes a spreading drive (65-67, 73) supported in the piston-actuating plunger (60) and includes spreading parts (67), which upon activation release the draw hooks (21) from the plunger disc (73).

3. The disposable injector according to claim 2, wherein the piston-actuating plunger (60) comprises several components.

4. The disposable injector according to claim 1, wherein the piston-actuating plunger (60) is non-rotatably supported in the housing (10).

5. The disposable injector according to claim 1, wherein on the housing (10) and/or on the actuating unit (80) a retention element (95) is arranged, which secures the piston-actuating plunger (60) in a locked position (8).

6. The disposable injector according to claim 1, wherein the upper, free end of the compression rod (65) projects up out of the bore (68), the actuation unit (80) further comprises a pushbutton (81) mounted in operative relationship with the shaft (66) of the compression rod (65).

* * * * *